United States Patent
Pelissier et al.

(10) Patent No.: US 8,491,479 B2
(45) Date of Patent: Jul. 23, 2013

(54) ULTRASONIC IMAGING SYSTEM HAVING COMPUTER COUPLED TO RECEIVE AND PROCESS RAW DATA

(75) Inventors: Laurent Pelissier, Vancouver (CA); Kris Dickie, Vancouver (CA); Trevor Hansen, Vancouver (CA); Chris Cheung, Burnaby (CA)

(73) Assignee: Ultrasonix Medical Corporation, Richond, BC (CA)

( * ) Notice: Subject to any disclaimer, the term of this patent is extended or adjusted under 35 U.S.C. 154(b) by 598 days.

(21) Appl. No.: 11/616,815

(22) Filed: Dec. 27, 2006

(65) Prior Publication Data

US 2007/0232915 A1  Oct. 4, 2007

Related U.S. Application Data

(60) Provisional application No. 60/744,193, filed on Apr. 3, 2006.

(51) Int. Cl.
*A61B 8/00* (2006.01)

(52) U.S. Cl.
USPC ............ 600/443; 600/407; 600/437; 600/441

(58) Field of Classification Search
USPC .......................... 600/437, 407, 441, 443–447
See application file for complete search history.

(56) References Cited

U.S. PATENT DOCUMENTS

| | | | |
|---|---|---|---|
| 4,965,572 A * | 10/1990 | Adamson | 340/968 |
| 6,263,094 B1 * | 7/2001 | Rosich et al. | 382/128 |
| 6,755,787 B2 * | 6/2004 | Hossack et al. | 600/447 |
| 6,780,149 B1 * | 8/2004 | Schulte | 600/1 |
| 7,254,494 B2 * | 8/2007 | Botter | 702/48 |
| 7,819,805 B2 | 10/2010 | Davies et al. | |
| 7,850,611 B2 | 12/2010 | Davies et al. | |
| 7,862,508 B2 | 1/2011 | Davies et al. | |
| 2003/0097068 A1 * | 5/2003 | Hossack et al. | 600/443 |
| 2007/0060817 A1 | 3/2007 | Davies | |
| 2007/0066894 A1 * | 3/2007 | Bartol et al. | 600/437 |

\* cited by examiner

*Primary Examiner* — Tse Chen
*Assistant Examiner* — Vani Gupta

(57) ABSTRACT

An ultrasound machine is configured for developing new modes for obtaining images or other useful information from ultrasound signals. The machine has a data processor configured to control a transmit circuit to generate ultrasound signals. Echo signals are received and digitized to yield RF data that is stored in a memory accessible to the data processor. A user can operate design mode application software to change the manner in which the RF data is processed to yield images or other useful information. New modes can be developed rapidly. The data processor may comprise a conventional personal computer equipped with suitable interfaces. An ultrasound machine may include and use a floating point processor for processing ultrasound signals.

14 Claims, 3 Drawing Sheets

ULTRASONIC IMAGING SYSTEM HAVING COMPUTER COUPLED TO RECEIVE AND PROCESS RAW DATA

REFERENCE TO RELATED APPLICATION

This application claims the benefit under 35 U.S.C. §119 of U.S. application Ser. No. 60/744,193 filed 3 Apr. 2006 which is hereby incorporated herein by reference.

TECHNICAL FIELD

This invention relates to ultrasonic imaging methods and apparatus. The invention may be applied to medical ultrasonic imaging.

BACKGROUND

Ultrasound imaging devices as used, for example in medical ultrasound imaging comprise a transducer, an electronic controller, and a user interface. The transducer typically comprises an array of piezoelectric transducer elements. Different transducers have different arrangements of elements. The electronic controller drives the transducer and collects and processes data from the transducer to generate, store, display and manipulate images. The user interface may include various input/output devices which allow a user to control the operation of the ultrasound system.

Ultrasound examinations are non-destructive and versatile and can provide high quality images.

The nature and quality of ultrasound images depends upon both the signals that drive individual transducer elements and the way in which reflected signals detected by the transducer elements are processed. A typical ultrasound machine may be configured to permit a user to select one of a few predefined imaging modes.

There remains a need for tools that are useful in the development of new ultrasound imaging modalities. There is also a need for sophisticated and yet cost-effective ultrasound machines.

SUMMARY

The following embodiments and aspects thereof are described and illustrated in conjunction with systems, tools and methods which are meant to be exemplary and illustrative, not limiting in scope.

One aspect of this invention provides ultrasound machines that are configured in a manner that facilitates the development of new ultrasound imaging modalities. Another aspect of the invention provides ultrasound machines that take advantage of powerful processing capabilities of a general purpose computer to enable sophisticated modes of operation. Another aspect of the invention provides ultrasound machines that utilize a floating point processor of a general purpose computer to perform signal processing functions which may include digital filtering and/or computing Doppler signals.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive. In the attached drawings.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
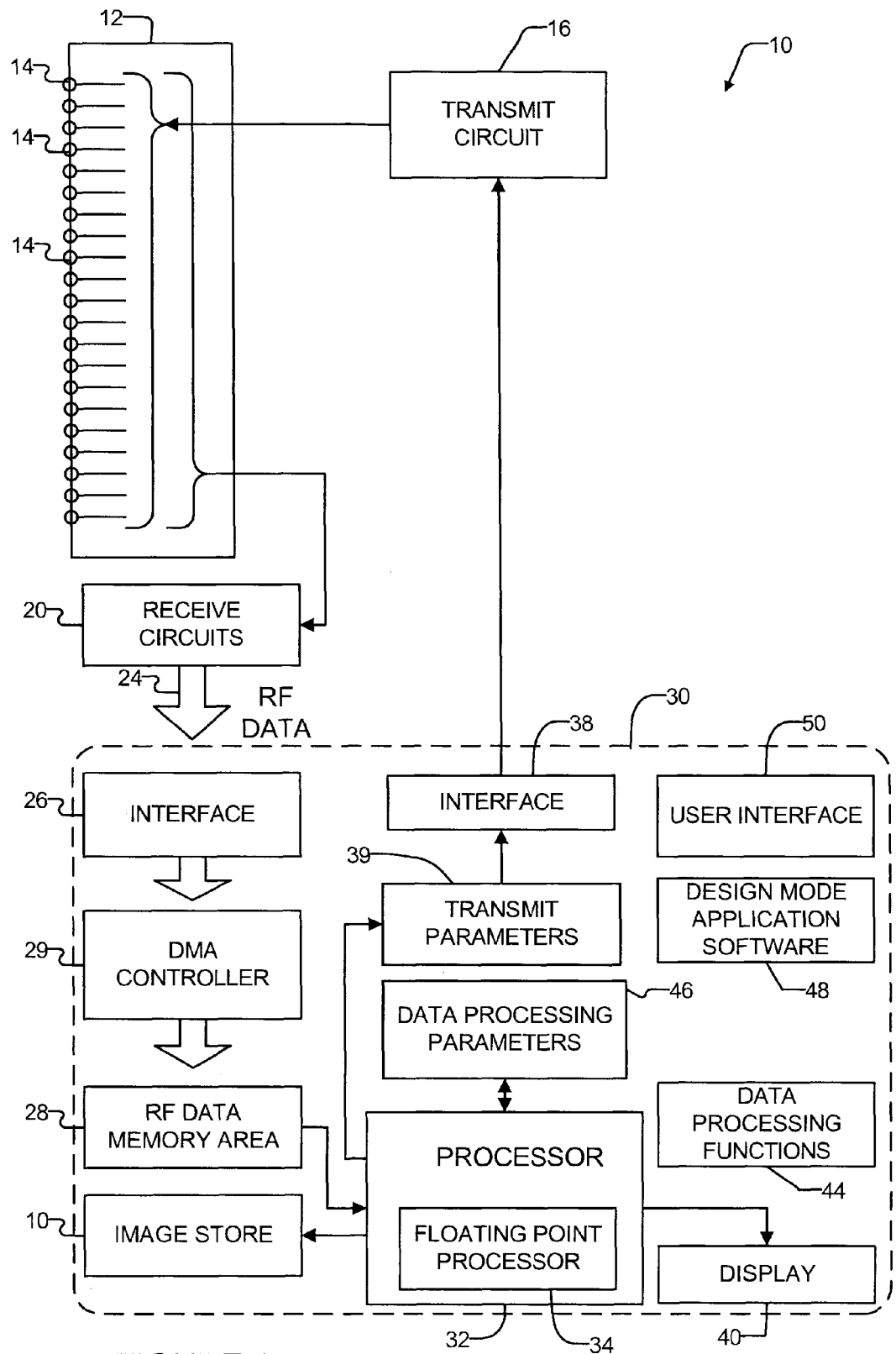
FIG. 1 is a block diagram illustrating an ultrasound machine according to one embodiment of the invention.

FIG. 1 is a block diagram of an ultrasound machine 10 according to one embodiment of the invention. Ultrasound machine 10 comprises a transducer 12 comprising a plurality of elements 14. While only a few elements 14 are shown in FIG. 1, a typical ultrasound transducer 12 may comprise several hundred elements. Each element 14 is coupled to a transmit circuit 16. Transmit circuit 16 generates electrical driving signals that are applied to transducers 14 to produce ultrasound signals.

The ultrasound signals propagate from the transducer and interact with the material of a body being examined. As a result, ultrasound is reflected back toward transducer 12. The reflected ultrasound is received at elements 14 and converted into electrical signals. The electrical signals are delivered to receive circuits 20.

Receive circuits 20 condition the electrical signals (for example, the receive circuits 20 may include suitable filters to remove various noise components from the signals and amplifiers to increase the amplitude of the signals. Receive circuits 20 include analog to digital converters (ADCs) that convert the signals into digital values. The ADCs sample the signals at a rate sufficient to obtain both phase and amplitude information for each signal. The resulting digital data, which may comprise raw samples of waveforms received at each element 14, may be termed RF data 24.

RF data 24 is delivered to a data processor 30, which may comprise a suitably-programmed computer workstation such as a personal computer, by way of a suitable hardware/software interface 26. The volume of RF data 24 will depend upon factors such as the rate at which data is sampled, the sampling resolution, the number of elements 14 in transducer 12 and the like. In a typical case, RF data is generated in 16-bit samples at a rate of 40 MHz and delivered to data processor 30 in real time. RF data 24 is delivered over a data bus capable of carrying the RF data in real time. Any suitable high-speed bus technology may be used to implement the transfer of RF data 24 to data processor 30. Once received in data processor 30, RF data 24 is stored in a RF data memory area 28 by a direct memory access (DMA) controller 29. RF data memory area 28 may be a portion of a main memory of data processor 30.

Data processor 30 comprises one or more microprocessors 32. The microprocessors may be, for example, Intel™ Pentium™ or AMD Athlon™ microprocessors. Data processor 30 also includes one or more floating point processors 34. Floating point processors 34 are conveniently integrated with microprocessor(s) 32. For example, the microprocessors referred to above have integral floating point processors.

Data processor 30 controls the operation of transmit circuit 16 by way of an interface 38. Data processor 30 includes a parameter store 39 that contains parameters that control the timing and/or waveforms of the driving signals to be delivered to elements 14 of transducer 12. The number and precise nature of the parameters in parameter store 39 will depend on the structure of transmit circuit 16 and upon how many different ways transmit circuit 16 can be adjusted to vary the driving signals to be delivered to elements 14.

Data processor 30 is also configured to process RF data from RF data memory area 28 to yield images that can be displayed on a display 40. Display 40 may be a high resolution computer monitor driven by data processor 30 by way of a suitable graphics interface. The graphics interface may comprise, for example, a graphics card and compatible software drivers.

Data processor 30 processes RF data received from transducer 12 to yield computed information and/or images. One example of computed information is a maximum blood flow velocity obtained by processing the RF data to yield information regarding the Doppler shift of reflected ultrasound signals.

Processor 32 processes the RF data according to one or more data processing functions 44. Data processing parameters 46 are provided for some or all of the data processing functions. The data processing parameters control the operation of the functions as described in more detail below.

Design mode application software 48 can be executed by processor 32 and permits users to control transmit parameters 39, select data processing functions 44, and select data processing parameters 46 for the selected data processing function 44. A user can interact with design mode application software 48 by way of a suitable user interface 50 which may comprise a keyboard, graphical user interface, some combination thereof, or any other suitable user interface.

Design mode application software 48 permits users to efficiently develop new ultrasound imaging modalities. A user can first set transmit parameters 39 to provide a desired set of driving signals for elements 14 of transducer 12. The user may specify a sequence of driving signals to be applied to each element 14 to yield a sequence of ultrasonic signals as desired for an ultrasound modality that the user is developing.

The driving signals applied to different ones of elements 14 may differ in various ways to achieve transmitted ultrasound signals that have desired characteristics. There are a wide variety of ways in which it is possible to vary the driving signals. Different driving signals may be applied to different elements 14 of transducer 12. For example:

elements 14 may be divided into groups in various ways and the same driving signals may be applied to all of the elements 14 in each group or the driving signals may be varied in a specified way for different ones of the elements in each group.

the phase of a driving signal may be varied in some specified manner either within a group of elements 14 or across all elements 14.

the waveforms of the driving signals applied to elements 14 may be varied.

the amplitudes of the driving signals applied to elements 14 may be varied.

the frequency of the driving signals applied to elements 14 may be varied.

the rate at which different driving signals are applied to elements 14 may be varied.

There are a virtually infinite number of different driving signals that could be delivered to cause the elements of a transducer to generate ultrasound. A user designing a new ultrasound mode may select a set of driving signals that appear to be appropriate for the selected mode.

Transmit parameters 39 may include, without limitation, parameters that specify:

a waveform, or waveforms, for the driving signals;

amplitudes for the driving signals;

relative phase shifts for driving signals to be applied to different elements 14;

frequencies for the driving signals;

rates at which the driving signals should be repeated;

focal point(s); and, depth.

A user designing a new ultrasound mode may select transmit parameters 39 to generate a set of driving signals that cause transducer 12 to emit ultrasound signals that appear to be appropriate for the selected mode. The user may also select an existing data processing function or design a new data processing function to extract desired information, whether an image or some other information, from the RF data that represents the ultrasound signals that are reflected from a body upon application of the driving signals to transducer 12. The data processing function may have many forms. Typical data processing functions involve operations such as beamforming, summing, and filtering to obtain preprocessed data that comprises echo amplitude information and/or other information useful for some diagnostic purpose.

The user can readily test and modify the ultrasound mode until the user is satisfied with the results obtained. The user can then save information that specifies the mode of operation for future use.

Figure 2:
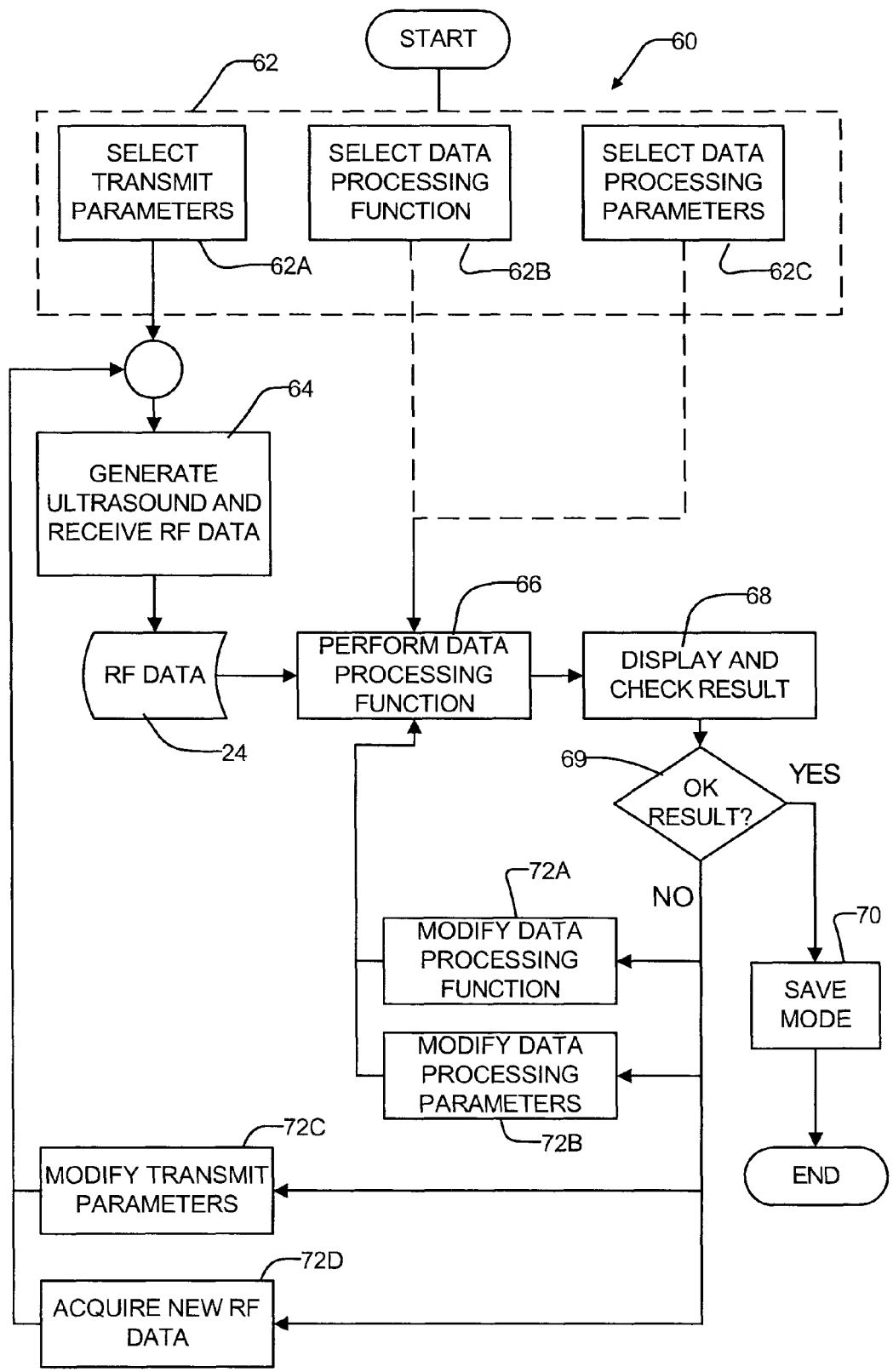
FIG. 2 is a flow chart illustrating a method according to the invention.

FIG. 2 shows a method 60 that may be practiced using apparatus 10 to develop new ultrasound modes. Method 60 begins at block 62 by permitting a user to specify both the nature of the transmitted ultrasound signals and the way in which received echo signals will be processed to yield an image or other information. In the illustrated embodiment, block 62 permits the user to select: transmit parameters 39 at block 62A; a data processing function 44 at block 62B; and data processing parameters 46 for the selected data processing function 44 at block 62C.

At block 64, the user causes system 10 to emit ultrasound signals according to the selected transmit parameters 39 and to acquire and store corresponding RF data 24. Method 60 continues at block 66 by applying the selected data processing function 44 to RF data 24 using the selected data processing parameters 46 to obtain a result.

In block 68 the result is displayed and checked. If the check indicates that the result is acceptable ("YES" result at block 69) then information specifying the mode is saved at block 70 and method 60 ends. If the check indicates that the result is not acceptable ("NO" result at block 69) then the user has the option of modifying the data processing function at block 72A or modifying the data processing parameters 46 at block 72B or modifying transmit parameters 39 at block 72C.

If the user elects to modify data processing function 44 or data processing parameters 46 then it is not necessary to acquire fresh RF data 24. The user can rapidly try the effect of different data processing functions and/or different data processing parameters on the results obtained without acquiring new RF data 24. In the alternative, apparatus 10 may be configured to acquire new RF data 24 each time block 72A or 72B is executed or a function may be provided to allow the user to cause apparatus 10 to acquire fresh RF data 24 as indicated, for example, by block 72D).

If the user elects to execute block 72C then method 60 acquires fresh RF data using the transmit parameters, as modified by the user in block 72C.

It can be appreciated that method 60 provides a very efficient way to develop and fine-tune new ultrasound operating modes. The operating modes may be any of:

B-mode imaging modes;
B/M imaging modes;
compound imaging modes;
harmonic imaging modes;
A-mode ultrasound;
Doppler imaging modes;
pulsed Doppler modes;
M-modes;
elastography modes;
other known types of imaging mode; or
new imaging modes.

Where data processor 30 comprises a personal computer running a common operating system then developing new data processing functions 44 is facilitated. The full range of computer programming tools that have been developed for programming such computers can be applied to write new data processing functions 44, as desired. For example, new data processing functions 44 may be built, developed, and run using an environment such as Microsoft™ Visual Studio or Matlab™. Data processor 30 may execute software that provides an application programming interface (API) that permits user software (such as software written in a language such as C++) to access RF data 24 and/or to control ultrasound machine 10. The data processing functions may perform customized signal processing, carry out special echo acquisition sequences or the like.

It is not necessary for data processing functions 44 to be entirely self-contained. Data processor 30 may contain software or software and hardware that provides certain standard processing of raw data 24. A data processing function 44 may take advantage of such standard processing and further process the data as required for the ultrasound mode being developed.

Figure 3:
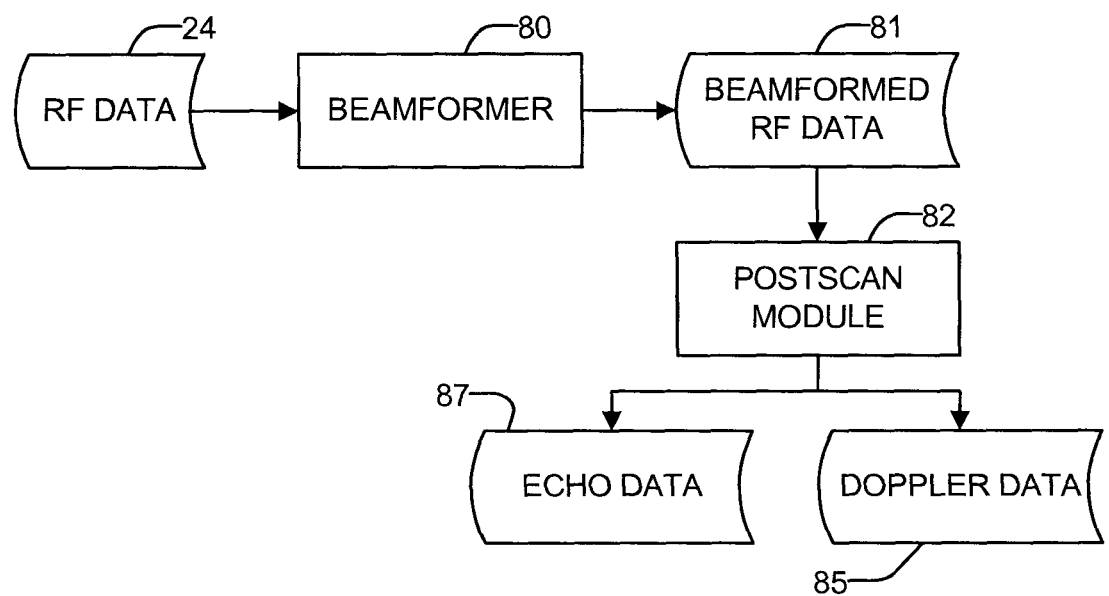
FIG. 3 is a schematic diagram illustrating a data stream passing through several data processing modules.

As shown in FIG. 3, data processor 30 may comprise a beamforming module 80 that processes RF-data 24 to yield pre-scan converted data 81; a module 82 that produces post-scan converted data 84 comprising both a Doppler data stream 85 and an echo data stream 87. Data processing functions 44 may access any of these sets of data as required. Data processing parameters 46 may affect the operation of these standard processing modules.

In some embodiments, apparatus 10 can be selectively operated either as a research platform, as described above, or as a diagnostic ultrasound machine. When apparatus 10 is being operated as a diagnostic ultrasound machine, only pre-configured standard operating modes are available for selection. The user can select an operational mode and may be able to adjust the operation of the selected mode by setting values for a limited predetermined set of parameters.

When apparatus 10 is switched to operate as a research platform, as described above, apparatus 10 preferably displays a noticeable warning that the apparatus is being operated in research mode so that users will not accidentally attempt to use the apparatus 10 to perform a standard ultrasound test, with possible unintended consequences. The warning may comprise a symbol or other indicia displayed on display 40 and/or a warning lamp or the like on user interface 50.

In some embodiments of the invention, data processing functions 44 for a preconfigured operational mode or for a mode under development include floating point computations that are performed by floating point processor(s) 34. Implementing filters using floating point arithmetic can yield a significant noise reduction and increased signal-to-noise ratio as compared to equivalent filters implemented using integer arithmetic. Implementing the processing for Doppler imaging using floating point arithmetic permits a large increase in dynamic range, especially when digital filtering is performed using floating point arithmetic using the floating point processor 34. Using a fast floating point processor can provide dramatic and surprising improvements in the quality of ultrasound images and/or other information derived from processing ultrasound signals. Where data processor 30 is a computer workstation, such as a personal computer, the floating point processor(s) 34 are included in the processor of data processor 30 thus rendering expensive separate processors unnecessary.

While a number of exemplary aspects and embodiments have been discussed above, those of skill in the art will recognize certain modifications, permutations, additions and sub-combinations thereof. For example, signals may be processed at receive circuit 20 in a way which preserves phase and amplitude information of reflected signals. The inventions disclosed herein include all such modifications, permutations, additions and sub-combinations as are within their true spirit and scope.

What is claimed is:

1. An ultrasound machine comprising:
a graphical display;
a transducer comprising a plurality of elements;
a transmit circuit connected to supply driving signals to the elements of the transducer;
a receive circuit connected to receive echo signals from the elements of the transducer;
a data processor connected to configure the transmit circuit according to the transmit parameters, wherein the transmit parameters include at least one of: a waveform for at least one driving signal; amplitudes for driving signals; relative phase shifts for driving signals to be applied to different elements of the transducer; frequencies for the driving signals; repetition rates for the driving signals and one or more focal points for a transmitted ultrasound signal;
a memory accessible to the processor and connected to receive and store pre-beamformed RF data representing the echo signals;
wherein the data processor comprises a processor and software instructions accessible for execution by the processor, the software instructions comprising design mode software instructions that, when executed by the processor, cause the processor to:
permit user selection of values for the transmit parameters;
provide an application programming interface configured to permit user software to access the pre-beamformed RF data and to control aspects of operation of the ultrasound machine;
permit user selection of a data processing function and selection of values for parameters of the selected data processing function, wherein user software that uses the application programming interface is available for selection as the selected data processing function;
configure the transmit circuit according to the selected values for the transmit parameters and trigger the transmit circuit to supply the driving signals to the transducer;
apply the user-selected data processing function to process the pre-beamformed RF data according to the selected values for the data processing parameters to produce an image; and,
display the image on the graphical display;
the software instructions further comprising instructions that:
provide one or more preconfigured operating modes;
in response to user input by way of a user control, switch between operation of the ultrasound machine as a research platform and operation of the ultrasound machine as a diagnostic ultrasound machine wherein, when the ultrasound machine is switched to operate as a diagnostic ultrasound machine only the preconfigured operating modes are available for selection by a user and user software that uses the application programming interface is not available for selection and, when the ultrasound machine is switched to operate as a research platform, the design mode software instructions are enabled for execution; and, activate a warning indicator when the ultrasound machine is switched to operate as a research platform.

2. An ultrasound machine according to claim 1 wherein the design mode software instructions comprise instructions that, when executed by the processor, cause the processor to:

permit user selection of modified values for the transmit parameters;

configure the transmit circuit according to the selected transmit parameters values and trigger the transmit circuit to supply the driving signals to the transducer to obtain fresh pre-beamformed RF data; and, apply the user-specified data processing function to process the fresh pre-beamformed RF data to produce a fresh image.

3. An ultrasound machine according to claim 1 wherein the transmit parameters include a waveform for at least one driving signal.

4. An ultrasound machine according to claim 1 wherein the transmit parameters include one or more focal points for a transmitted ultrasound signal.

5. An ultrasound machine according to claim 1 wherein the data processor comprises a personal computer and the processor comprises a microprocessor of the personal computer.

6. An ultrasound machine according to claim 1 wherein the microprocessor comprises a floating point processor.

7. An ultrasound machine according to claim 6 wherein the user-specified data processing function includes a filtering stage and the filtering stage is implemented by floating point arithmetic instructions accessible for execution by the floating point processor, the floating point arithmetic instructions comprising instructions that, when executed by the floating point processor, cause the floating point processor to perform the filtering stage.

8. An ultrasound machine according to claim 6 wherein the user-specified data processing function includes a Doppler processing stage and the Doppler processing stage is implemented by floating point arithmetic instructions accessible for execution by the floating point processor, the floating point arithmetic instructions comprising instructions that, when executed by the floating point processor, cause the floating point processor to perform the Doppler processing stage.

9. An ultrasound machine according to claim 1 wherein the warning indicator comprises one or more of a symbol or other indicia displayed on a display and a warning lamp.

10. An ultrasound machine according to claim 1 comprising a high speed data bus connected to deliver the pre-beamformed RF data from the receive circuit to the memory wherein the software instructions cause the pre-beamformed RF data to be retained in the memory while causing the processor to apply a plurality of user-specified data processing functions to process the pre-beamformed RF data.

11. A method for establishing an ultrasound imaging protocol, the method comprising:

receiving information comprising transmit parameters specifying driving signals to be applied to elements of a transducer wherein the transmit parameters include at least one of: a waveform for at least one driving signal; amplitudes for driving signals; relative phase shifts for driving signals to be applied to different elements of the transducer; frequencies for the driving signals; repetition rates for the driving signals and one or more focal points for a transmitted ultrasound signal;

applying the driving signals to the elements of the transducer;

detecting echo signals and storing pre-beamformed RF data representing the echo signals in a memory accessible to the processor; and, in the processor, generating a plurality of different images from the stored pre-beamformed RF data by: executing a user-specified data processing function according to a user-specified set of data processing parameters to process the stored pre-beamformed RF data to generate an image wherein the user-specified data processing function comprises user software accessing the stored pre-beamformed RF data by way of an application programming interface and display the image; and, one or more times, modifying the user software and applying the modified user software to process the stored pre-beamformed RF data to yield a modified image and display the modified image; and, receiving user input modifying one or more of the transmit Parameters and, in response to the modification of the transmit Parameters, acquiring and storing fresh pre-beamformed RF data by applying the modified transmit parameters to generate modified driving signals and applying the modified driving signals to the elements of the transducer and applying the user software or the modified user software to process the stored fresh pre-beamformed RF data to generate another image and displaying the another image.

12. An ultrasound machine according to claim 1 wherein the software instructions comprise instructions that when executed by the processor, cause the processor to: prompt a user to store the user-specified data processing function in the memory.

13. An ultrasound machine according to claim 1 wherein the software instructions comprise instructions that when executed by the processor, cause the processor to: prompt a user to store the user-specified values for the transmit parameters.

14. A method for establishing an ultrasound imaging protocol according to claim 11, the method comprising for each of the generated images:

prompting a user to store the user-specified data processing function and user-specified set of data processing parameters corresponding to the generated image.

* * * * *